United States Patent [19]

Patel

[11] Patent Number: 5,978,443
[45] Date of Patent: Nov. 2, 1999

[54] AUTOMATED REMOVAL OF BACKGROUND REGIONS FROM RADIOGRAPHIC IMAGES

[75] Inventor: Maqboolahmed S. Patel, Waukesha, Wis.

[73] Assignee: General Electric Company, Milwaukee, Wis.

[21] Appl. No.: 08/967,553

[22] Filed: Nov. 10, 1997

[51] Int. Cl.[6] ................................................. G01N 23/04
[52] U.S. Cl. ............................................. 378/62; 378/98.7
[58] Field of Search ................................. 378/62, 98, 98.7

[56] References Cited

U.S. PATENT DOCUMENTS

| | | | |
|---|---|---|---|
| 4,731,863 | 3/1988 | Sezan | 382/51 |
| 4,804,842 | 2/1989 | Nakajima | 250/327.2 |
| 4,829,181 | 5/1989 | Shimura | 250/327.2 |
| 4,851,678 | 7/1989 | Adachi | 250/327.2 |
| 4,859,850 | 8/1989 | Funahashi | 250/327.2 |
| 4,868,651 | 9/1989 | Chou et al. | 378/98.7 |
| 4,891,757 | 1/1990 | Shroy, Jr. et al. | 378/98.7 |
| 4,962,539 | 10/1990 | Takeo | 382/9 |
| 4,967,079 | 10/1990 | Shimura | 250/327.2 |
| 5,028,782 | 7/1991 | Nakajima | 250/327.2 |
| 5,268,967 | 12/1993 | Jang | 382/6 |

OTHER PUBLICATIONS

Jiebo Luo and Robert A. Senn; Collimation detection for digital radiograp.; pp. 74–85, SPIE vol. 3034, 1997.

*Primary Examiner*—David Vernon Bruce
*Attorney, Agent, or Firm*—Quarles & Brady; Christian G. Cabou; Phyllis Y. Price

[57] ABSTRACT

An x-ray system acquires medical images stored as an array of pixel values. Bright regions in the image produced by collimation or protective devices on the patient are automatically detected and filled with dark pixel values to reduce glare and improve the readability of the image. Automatic detection is achieved on a down sampled copy of the image in which edges of bright background regions are detected. The bright background regions in the down sampled image are filled with dark pixel values and an up sampled copy of this filled image is merged with the original image to produce the final image.

14 Claims, 3 Drawing Sheets

AUTOMATED REMOVAL OF BACKGROUND REGIONS FROM RADIOGRAPHIC IMAGES

BACKGROUND OF THE INVENTION

The field of the invention is medical imaging, and particularly, the processing of digitized medical images.

There are a number of medical imaging systems in use today which produce images in the form of digitized data arrays. Such systems may use x-rays, ultrasound, magnetic resonance, positron emission, or gamma ray emission as the modality for acquiring the image data. Regardless of the modality used to acquire it, once the image is digitized as an array of pixel intensity values, it can be processed using filters and image enhancers to improve the diagnostic quality of the image.

While the field of view of the imaging system can be controlled during image acquisition to focus on the anatomy of interest to the diagnostician, sometimes considerable background is included in the image. If the background is very bright, it can be very distracting and a hindrance to an accurate reading of the image. For example, x-ray images are often acquired with collimators placed on the machine or the patient to limit the amount of radiation reaching unintended anatomical regions. Collimators basically reduce the amount of radiation reaching the area shadowed by them. As a result, the region covered by the collimators is highly attenuated and appears bright on the final image. When such an image is viewed on a view box by a radiologist, the bright areas in the image can be quite significant and hence create a glare. This glare is very discomforting to the radiologist and can affect adversely the film reading ability of the radiologist. If the bright areas caused by the collimation can be eliminated from the image, the accuracy of reading the film can be improved.

Methods previously used to detect and remove bright background regions from medical images are either very computationally expensive, not very robust, or require considerable manual input. Such methods are described by Jiebo Luo, et al. "Collimation Detection For Digital Radiology", SPIE Vol. 3034 (1997) and the publications referred therein.

SUMMARY OF THE INVENTION

The present invention is a method for automatically detecting bright background regions in a medical image and changing the brightness to a diagnostically acceptable level. More particularly, the method includes producing a down sampled copy of the image array, detecting the location of edges in the down sampled image, filling bright regions defined by edges with predetermined brightness level values; producing an up sampled copy of the filled image, and merging the filled regions in the up sampled copy of the filled image with corresponding regions in the image array.

A general object of the invention is to provide an automatic method for changing the brightness of background regions in a medical image. No human intervention is required by the invented method. The image is divided into regions by detecting edges and the bright background regions are then identified. The bright background regions are filled with diagnostically acceptable brightness levels.

Another object of the invention is to reduce the computational burden of the method. This is achieved in part by the down sampling step which reduces the size of the array on which the computationally intense steps are performed.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
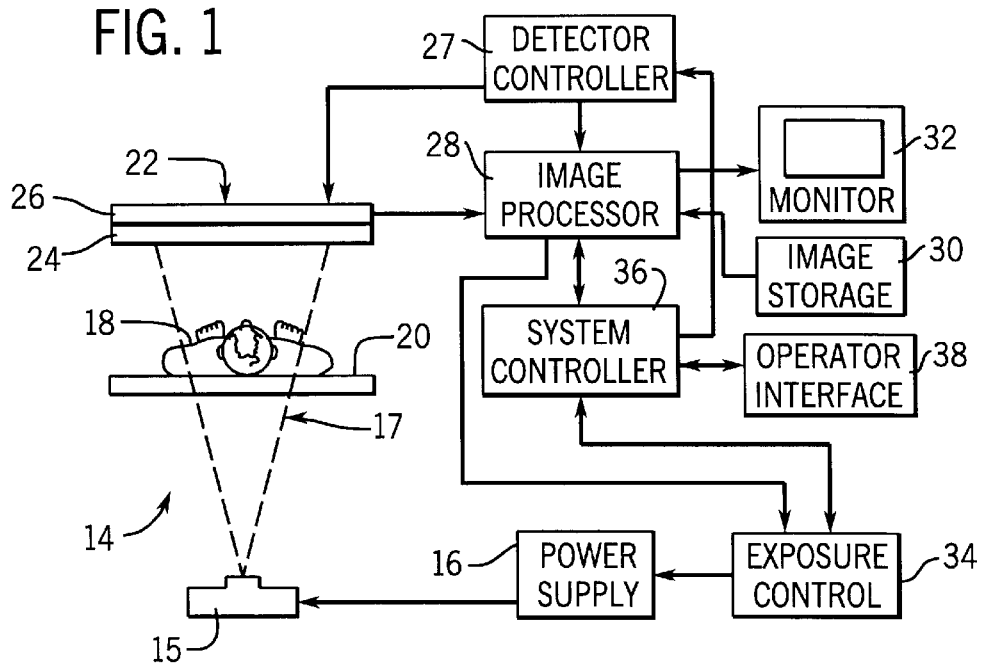
FIG. 1 is an electrical block diagram of an x-ray system which employs the present invention.

With initial reference to FIG. 1, an x-ray apparatus 14 includes an x-ray tube 15 which, when excited by a power supply 16, emits an x-ray beam 17. As illustrated, the x-ray beam is directed toward a patient 18 lying on an x-ray transmissive table 20. The portion of the beam which is transmitted through the table and the patient impinges upon an x-ray detector designated 22. The x-ray detector 22 comprises a scintillator 24 that converts the x-ray photons to lower energy photons in the visible spectrum. Contiguous with the scintillator 24 is a photodetector array 26, which converts the light photons into an electrical signal. A detector controller 27 contains electronics for operating the detector array to acquire an image and to read out the signal from each photodetector element.

The output signals from the photodetector array 26 are coupled to an image processor 28 that includes circuitry for digitizing each signal and storing the digitized signals as an image array. Each digitized signal indicates by its level the attenuation of the x-rays passing through the patient 18 and the brightness of a pixel in the processed image. The processed image is displayed on a video monitor 32 and may be archived in an image storage device 30. The image processor 28 additionally produces a brightness control signal which is applied to an exposure control circuit 34 to regulate the power supply 16 and thereby the x-ray exposure.

The overall operation of the x-ray apparatus 14 is governed by a system controller 36 which receives commands from the x-ray technician via an operator interface panel 38.

Figure 3:
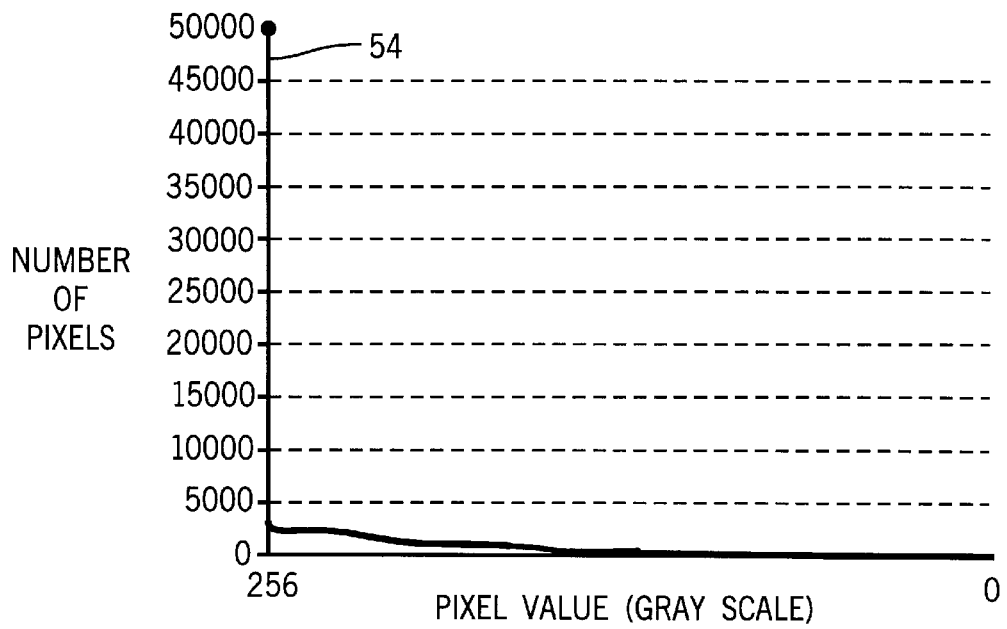
FIG. 3 is a graphic representation of a histogram produced by the system of FIG. 1.
Figure 2:
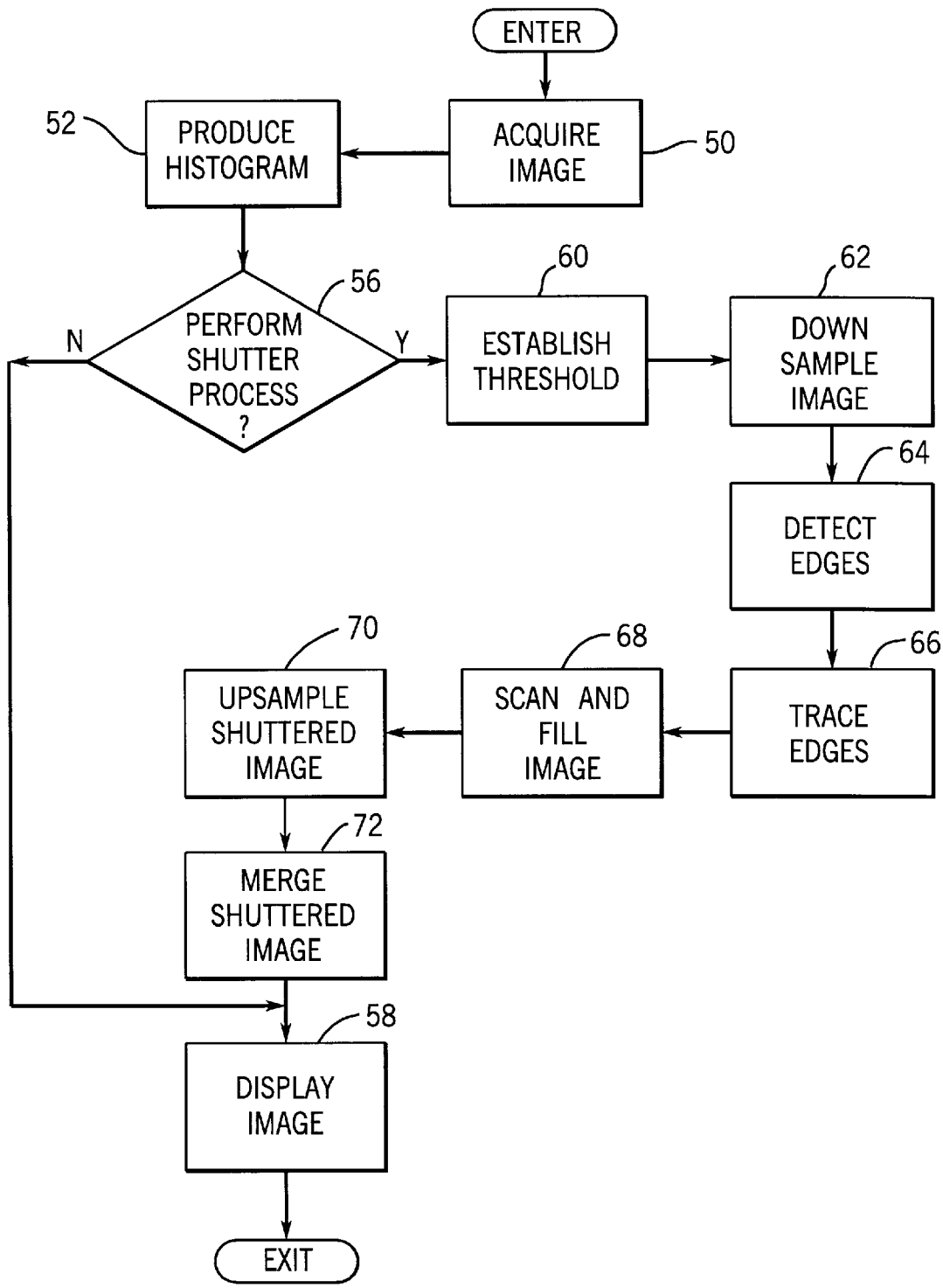
FIG. 2 is a flow chart illustrating the steps performed by the x-ray system of FIG. 1 to practice the preferred embodiment of the invention.

The operation of the x-ray system is best explained with reference to the flow chart in FIG. 2. As indicated by process block 50, the first step is to acquire an x-ray image by operating the power supply 16 in accordance with the prescription entered by the operator. The resulting 2 k by 2 k pixel digitized image is stored and a histogram is produced from the image as indicated at process block 52. As is well known in the art, a histogram is a count of the number of image pixels at each possible brightness level, and it indicates the prevailing brightness levels in the image. When there is a significant bright background region in the image there is a sharp peak in the histogram as indicated at 54 in FIG. 3.

Referring again to FIG. 2, the histogram is analyzed at decision block 56 and if a significant peak indicating bright background is detected, "shutters" are needed to block out the bright background regions. If no shutters are required, the system branches and the image is displayed at process block 58 in the conventional manner.

If the image needs shutters, the histogram is again examined at process block 60 to establish a threshold brightness level. The shutter threshold is set just below the brightness level of the background peak 54, and as will be described below, this level determines which regions in the image will be blacked out, or shuttered.

As indicated at process block 62, the first step in locating the background regions to be shuttered is to produce a down sampled copy of the image. This is accomplished by selecting one pixel value from each 5×5 pixel kernal over the entire 2 k by 2 k image, or by computing the average value of the pixels in each 5×5 pixel kernal. In the preferred embodiment the image is thus down sampled by a factor of five to reduce the 2 k by 2 k pixel image to a 400 by 400 pixel image. In addition, the 16-bit image intensity levels are truncated to 8-bit intensity levels in the down sampled copy. This down sampling reduces the computational burden of the steps to follow, and it removes from the image the thin edges which lie in the subject and which do not define the boundaries of the background.

As indicated at process block 64, the next step is to detect the edges in the down-sampled image using a Canny edge detector such as that described by John F. Canny, "*Finding Edges and Lines in Images*," MIT Artificial Intelligence Laboratory, Technical Report no. 702. The σ for the Gaussian filter used in the Canny operator is set to five to smooth out the unwanted edges and filter out noise in the image. What remains is a central region separated from surrounding background regions by intense edges. The remaining intense edges are then detected using an edge tracer with hysteresis as indicated at process block 66. This process is also described in the above-cited Canny publication at Section 3.4.

More specifically, in the preferred embodiment of the invention a Gaussian filter and its derivative in one dimension are produced using the following formula:

$$Gaussian(n) = \frac{1}{\sqrt{2\pi\sigma^2}} \exp\left(\frac{-n^2}{2\sigma^2}\right)$$

$$dGaussian(n) = \frac{1}{\sqrt{2\pi\sigma^2}} \left[\exp\left(\frac{-(n-1)^2}{2\sigma^2}\right) - \exp\left(\frac{-(n+1)^2}{2\sigma^2}\right)\right]$$

where: n=0.1, 1, . . . 19, and σ standard deviation is set to 5. The convolution of the image (n) with the Gaussian filter along each dimension is then performed to produce a smoothed image:

$$[x_{smooth}(n)]_{row} = [Gaussian(n)]_{row} * [image(n)]_{row},$$

$$[y_{smooth}(n)]_{col} = [Gaussian(n)]_{col} * [image(n)]_{col},$$

where * indicates the convolution operation.

The gradient of this smoothed image is then calculated along each axis:

$$[x_{der}]_{col} = [dGaussian(n)]_{row} * [x_{smooth}(n)]_{row},$$

$$[y_{der}]_{col} = [dGaussian(n)]_{col} * [x_{smooth}(n)]_{col},$$

The image of the edges is then produced as follows:

$$Norm(n) = \sqrt{(x_{der}(n))^2 + (y_{der}(n))^2}$$

and $P_{max}$ is set to the maximum value in Norm(n) and $P_{min}$ is set to the minimum value in Norm(n). A threshold value is calculated:

$$\text{Threshold} = \alpha(P_{max} - P_{min}) + P_{min},$$

and this threshold is used to produce the edge image as follows:

$$I_{edge} = Norm(n) \geq \text{Threshold}.$$

The edge image ledge is traced (with hysteresis) to link up the indicated edge points. The edge image ($I_{edge}$) is scanned until an edge point having a strength greater than $T_{high}$ is found which has not thus far been marked. Starting at this point, all connecting points in $I_{edge}$ which have a strength greater than $T_{low}$ are also marked as final edge points. This process of finding unmarked edge points that exceed $T_{high}$ and marking all connected edge points that exceed $T_{low}$ continues until the entire edge image $I_{edge}$ has been scanned and connecting edge points marked.

After the intense edges are detected, a filling process is performed at process block 68 in which the background regions are scanned and the pixels therein set to a black intensity level. This process uses the shutter threshold level acquired from the histogram in process block 60 described above, as well as the intense edges located in process block 66. This process is divided into eight separate scans. The first scan starts at the top left corner of the down sampled image and moves to the right until one of the detected edges is reached. The process continues in this manner by scanning each successive row of pixels until the bottom of the image is reached. For each scan line, the first few pixel levels are compared to the shutter threshold value to determine if the scan line is starting in a background region. If it is, all the pixels in the scan line up to the edge point are set to a dark level (zero in the preferred embodiment). Otherwise, the pixel levels are not changed.

Because it is possible for a break to occur in the detected edges that define the background regions, each of the eight separate scans are modified such that subsequent scan lines do not extend beyond previous scan lines. For example, if scan line 10 fills 60 pixels with dark background values then the subsequent scan lines 11–400 will not fill in background values beyond the 60th pixel from the image boundary. This prevents the process from filling into non-background regions when there is a break in the detected edge. As a result, however, the scan and fill process must be performed in eight separate scans rather than four.

Figure 4:
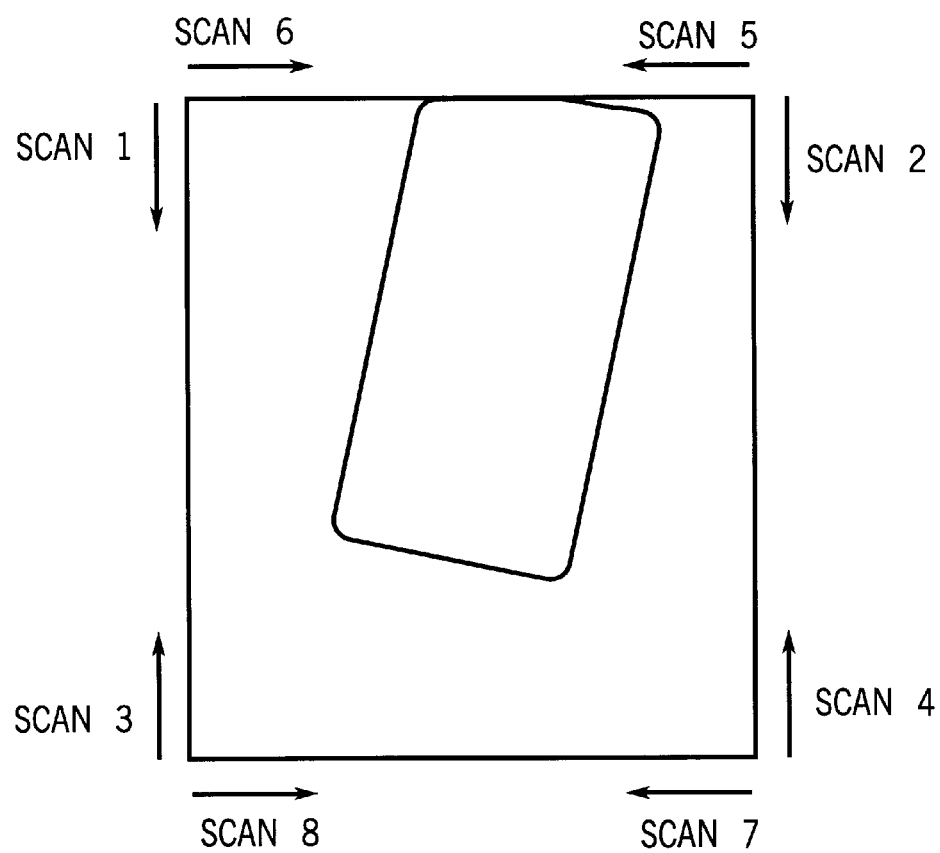
FIG. 4 is a schematic illustration of the scan and fill process which is one of the steps of FIG. 2.

Referring particularly to FIG. 4, the eight separate scans start at one of the four image corners and work in one of two directions:

scan 1—scan left to right and work from top to bottom;

scan 2—scan right to left and work from top to bottom;

scan 3—scan from left to right and work from bottom to top;

scan 4—scan from right to left and work from bottom to top;

scan 5—scan from top to bottom and work from right to left;

scan 6—scan from top to bottom and work from left to right;

scan 7—scan from bottom to top and work from right to left; and scan 8—scan from bottom to top and work from left to right.

The particular order in which the eight scans are performed is not important. The result of the eight scan and fill steps is that all the pixels in the background regions surrounding the subject are set to a dark level.

As indicated at process block 70 the scanned and filled image is then up-sampled back to the same size as the original image. This is a reverse of the down sampling step and is performed by setting each 5 by 5 block of pixels in the final 2 k by 2 k "shuttered image" to the value of its corresponding pixel in the 400 by 400 pixel scanned and filled image. The shuttered image is then merged with the original medical image to darken the collimated areas as indicate at process block 72. This is accomplished by darkening each pixel in the original image which corresponds to a darkened pixel in the shuttered image.

The final image is thus comprised of the original medical image with the surrounding collimated background regions set to a dark level. When this image is displayed at process 58, the radiologist can examine the anatomic regions of clinical interest without the glare of the surrounding background.

It should be apparent that a number of variations are possible from the preferred embodiment without departing from the spirit of the invention. For example, the present invention can be easily applied to any medical image embodied as a stored image array. For example, images produced by Fuji CR, digitized x-ray images may be shuttered using the present invention. While a Canny filter is employed in the preferred embodiment, many methods are known for detecting the strong edges in an image.

I claim:

1. A method for producing an image with a medical imaging system, the steps comprising:
   a) acquiring data from a patient and producing a digitized image data array from the acquired data;
   b) calculating a shutter threshold level from the image data which indicates the brightness level of background regions therein to be shuttered;
   c) producing a down sampled copy of the image data array;
   d) detecting the location of edges in the down sampled copy;
   e) filling in background regions in the down sampled copy, which regions are defined by the detected edges, and which regions have a brightness level greater than the shutter threshold level;
   f) producing an up sampled copy of the filled regions; and
   g) merging the filled regions in the up sampled copy with the corresponding regions in the digitized image data array to produce a final image in which the filled regions are set to a predetermined brightness level.

2. The method as recited in claim 1 in which the medical imaging system is an x-ray system and collimators are located in the field of view of the acquiring image data array.

3. The method as recited in claim 1 in which a histogram is produced from the image data array and the shutter threshold level is calculated from the histogram.

4. The method as recited in claim 1 in which a Canny filter is employed in step d).

5. The method as recited in claim 1 in which the background regions are filled in in step e) by setting the pixels therein to a preset value.

6. The method as recited in claim 5 in which the preset value is substantially zero.

7. A method for removing bright background regions in a digitized medical image of a subject, the steps comprising:
   a) producing a histogram from the digitized medical image;
   b) detecting from the histogram the presence of bright background regions in the digitized medical image;
   c) calculating a shutter threshold level from the histogram which indicates the brightness level of background regions in the digitized medical image that are to be shuttered;
   d) producing a down sampled copy of the digitized medical image;
   e) detecting the location of edges between the subject and background regions in the down sampled copy;
   f) filling in the background regions in the down sampled copy;
   g) producing an up sampled copy of the filled image; and
   h) merging the filled background regions in the up sampled copy with the corresponding regions in the digitized medical image to produce a final image in which the filled background regions are set to a predetermined brightness level.

8. The method as recited in claim 7 in which the digitized medical image is produced by an x-ray system and collimators are located in the field of view of the digitized medical image.

9. The method as recited in claim 7 in which a canny filter is employed in step e).

10. The method as recited in claim 7 in which step e) includes:
    i) applying an edge detector to the down sampled copy; and
    ii) tracing the detected edges to fill in gaps in the detected edges.

11. The method as recited in claim 7 in which step f) includes scanning the background regions and setting the pixels therein to a preset value.

12. The method as recited in claim 11 in which the scanning is performed line-by-line by starting at a boundary of the down sampled copy and setting pixels to the preset value until a detected edge is reached.

13. The method as recited in claim 12 in which the down sampled copy has a boundary comprised of four sides, and the scanning is performed from all four sides.

14. The method as recited in claim 11 in which the preset value results in a dark image pixel.

* * * * *